US006348204B1

(12) United States Patent
Touzan

(10) Patent No.: US 6,348,204 B1
(45) Date of Patent: Feb. 19, 2002

(54) COSMETIC OR DERMATOLOGICAL COMPOSITION CONTAINING AT LEAST ONE EXTRACT OF MULBERRY, AT LEAST ONE EXTRACT OF SKULLCAP AND AT LEAST ONE SALICYLIC ACID DERIVATIVE

(75) Inventor: Philippe Touzan, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/415,219

(22) Filed: Oct. 12, 1999

(30) Foreign Application Priority Data

Oct. 12, 1998 (FR) ............................................. 98 12747

(51) Int. Cl.⁷ .......................... A61K 7/02; A61K 7/135; A61K 35/78; A61K 31/19; A61K 31/60
(52) U.S. Cl. .......................... 424/401; 424/725; 424/62; 424/741; 424/773; 514/557; 514/844; 514/159; 514/947
(58) Field of Search .............................. 424/401, 195.1, 424/62, 741, 725, 773; 514/557, 844, 159, 947

(56) References Cited

U.S. PATENT DOCUMENTS 5,609,875 A  *  3/1997  Hadas
5,773,014 A     6/1998  Perrier et al.

FOREIGN PATENT DOCUMENTS

EP      0 747 043 A1    12/1996

OTHER PUBLICATIONS

Woodruff: "Lightening Skin and Lessening Cellulite" Manufacturing Chemist, Apr. 1996, pp. 38–41.
Patent Abstracts of Japan, vol. 098, No. 001 (C & JP 09 227353).

* cited by examiner

Primary Examiner—Diana Dudash
Assistant Examiner—Clinton Ostrup
(74) Attorney, Agent, or Firm—Oblon, Spivak, McClelland, Maier & Neustadt, P.C.

(57) ABSTRACT

A cosmetic or dermatological composition, comprising:
in combination, at least one extract of mulberry or an active substance isolated from the extract, at least one extract of skullcap or an active substance isolated from the extract and at least one salicylic acid derivative or salt thereof.

16 Claims, No Drawings

COSMETIC OR DERMATOLOGICAL COMPOSITION CONTAINING AT LEAST ONE EXTRACT OF MULBERRY, AT LEAST ONE EXTRACT OF SKULLCAP AND AT LEAST ONE SALICYLIC ACID DERIVATIVE

BACKGROUND OF THE INVENTION

1. Field of the Invention

The present invention relates to a cosmetic or dermatological composition containing, in combination, at least one extract of mulberry or an active substance isolated from such an extract, at least one extract of skullcap or an active substance isolated from such an extract, and at least one salicylic acid derivative. The present invention also relates to the use of the composition by topical application to the skin of the face and/or the body, with the objective of whitening or depigmenting the skin, of depigmenting head hair and/or other hair, or of treating skin pigmentation marks.

2. Description of the Background

The color of human skin depends on many different factors and, in particular, on the seasons of the year, race and sex, and it is mainly determined by the concentration and nature of the melanin produced by the melanocytes. In addition, at different periods in their lives, certain individuals develop darker and/or more colored marks on the skin, and more especially on the hands, which imparts heterogeneity to the skin. These marks also result from a large concentration of melanin in the keratinocytes located at the surface of the skin.

Similarly, the color of head hair and other hair results from melanin; when the head hair or other hairs are dark, certain people wish to have them lightened in color. This is particularly advantageous for hair which is less visible when light than when dark.

The mechanism of pigmentation of skin, head hair and other hair, that is to say the formation of melanin, is particularly complex and schematically involves the following main steps:

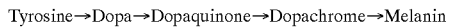

Tyrosine→Dopa→Dopaquinone→Dopachrome→Melanin

Tyrosinase is the essential enzyme involved in the above reaction sequence. In particular, tyrosinase catalyses the reaction for the conversion of tyrosine into dopa (dihydroxyphenylalanine) by virtue of its hydroxylase activity, and the reaction for the conversion of dopa into dopaquinone by virtue of its oxidase activity. Tyrosinase only acts when it is in the mature form, under the action of certain biological factors.

Tyrosinase is recognized as being depigmenting if it acts directly on the vitality of the epidermal melanocytes in which melanogenesis takes place and/or if it interferes with one of the steps in the biosynthesis of melanin, either by inhibiting one of the enzymes involved in melanogenesis or by becoming intercalated as a structural analogue of one of the chemical compounds in the synthetic chain of melanin, which chain can then become blocked and ensure the depigmentation.

The substances most commonly used as depigmenting agents particularly are hydroquinone and its derivatives, in particular its ethers such as hydroquinone monomethyl ether and monoethyl ether. Although these compounds have a certain efficacy, they are, unfortunately, not free of side effects because of the toxicity they entail, which can make them intricate, or even dangerous, to use. This toxicity arises from the fact that the compounds intervene in fundamental mechanisms of melanogenesis, killing cells which then risks disturbing the biological environment of the cells and which consequently obliges the skin to eliminate them by producing toxins.

Thus, hydroquinone is a compound which is particularly irritant and cytotoxic to melanocytes, and the total or partial substitution of this compound has been envisaged by those of skill in the art.

Substances have thus been sought which do not have any involvement in the melanogenesis mechanism, but which act upstream on tyrosinase by preventing its activation and are thus considerably less toxic.

The use of inoffensive topical depigmenting substances which are of good efficacy is most particularly desired in order to treat regional hyperpigmentations mediated by melanocyte hyperactivity such as idiopathic melasmas, which occur during pregnancy ("pregnancy mask" or chloasma) or in oestro-progestative contraception, localized hyperpigmentations mediated by hyperactivity and proliferation of benign melanocytes such as senile pigmentary marks known as actinic lentigo, accidental hyperpigmentations or depigmentations resulting from photosensitization and post-lesional cicatrization, as well as certain leucodermias such as vitiligo. For the latter it is possible for the cicatrization to result in a scar, giving the skin a whiter look, and leukodermias, failing the ability to repigment the injured skin. Depigmentation of the areas of residual normal skin is effected to give the skin an overall uniform white shade.

Thus, various whitening agents for human skin, head hair and/or other hair have been proposed which do not have the drawbacks of known compounds, i.e. which are non-irritant, non-toxic and/or non-allergenic to the skin and which are stable in a composition.

For example, patent EP-A-0,747,043 describes the use of alkyl salicylic acid derivatives as inhibitors of tyrosinase activity in a whitening or depigmenting composition. U.S. Pat. No. 5,580,549 also describes the use of alkyl and alkoxy salicylic acid derivatives at high concentrations or in combination with other depigmenting agents, for treating dyschromia.

Depigmenting cosmetic compositions comprising, as active principles, compounds which inhibit the activity of tyrosinase, obtained from extracts of bark, of the exudates or of the roots of mulberry, or sohakuhi, are also known as disclosed in C.A. Essential Oils, Cosmetics, vol. 88, 1978, page 227, abstract 88:65874z or JP-A-50 135,236. EP-A-0, 296,923 also discloses a composition with depigmenting activity comprising an extract of mulberry, or an active substance isolated from such an extract.

For its part, JP 06-107,532 relates to a cosmetic composition which prevents and treats pigmentation marks by inhibiting melanogenesis, which composition contains from 0.001 to 20% by weight of one or more extracts, including an extract of the root of Scutellaria baicalensis (skullcap) and an extract of mulberry bark, and 0.001 to 30% by weight of a UV absorbing agent and/or an agent for scattering UV rays.

A need continues to exist for a depigmenting or whitening composition which is more effective than the compositions mentioned above, while at the same time is well tolerated.

SUMMARY OF THE INVENTION

Accordingly, one object of the present invention is to provide a composition for cosmetic or dermatological use for the depigmentation or whitening of the human skin or hair which is better tolerated by the skin and hair and which is more effective than art known compositions.

Briefly, this object and other object of the present invention as hereinafter will become more readily apparent can be attained by a cosmetic and/or dermatological composition containing, in combination, at least one extract of mulberry or an active substance isolated from an extract, at least one extract of skullcap or an active substance isolated from an extract, and at least one salicylic acid compound of formula (I) or a salt thereof:

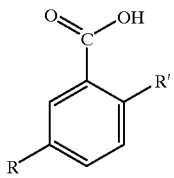

(I)

wherein R is hydrogen or a saturated or unsaturated, linear, branched or cyclic aliphatic, alkoxy, ester or ketoxy chain containing from 2 to 22 carbon atoms and optionally substituted with at least one substituent selected from the group consisting of halogen, trifluoromethyl and hydroxyl in free form or esterified with an acid containing from 1 to 6 carbon atoms or with a carboxyl group which is free or esterified with a lower alcohol containing from 1 to 6 carbon atoms; and R' is a hydroxyl group or an ester function of the formula:

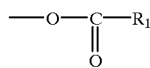

wherein $R_1$ is a saturated or unsaturated $C_{1-18}$-aliphatic group.

DETAILED DESCRIPTION OF THE PREFERRED EMBODIMENTS

In the salicylic acid formula above, substituent R preferably contains at least 4 carbon atoms. Preferred such groups are saturated linear alkyl or alkoxy radicals containing from 4 to 11 carbon atoms.

Advantageously, the salicylic acid derivative is selected from salicylic acid, 5-n-octanoylsalicylic acid, 5-n-decanoylsalicylic acid and 5-n-dodecanoyl-salicylic acid, particularly 5-n-octanoylsalicylic acid.

The salicylic acid compound may also be used in salt form, and in particular salts obtained by salification with a base. Suitable such bases include inorganic bases such as alkali metal hydroxides of which sodium hydroxide and potassium hydroxide are representative and ammonium hydroxides or, better still, organic bases.

Preferably, amphoteric bases are employed to salify the salicylic acid derivatives, i.e. bases which have both anionic and cationic functional groups.

The amphoteric bases include primary, secondary, tertiary and cyclic organic amines, and more especially amino acids. Suitable examples of amphoteric bases include glycine, lysine, arginine, taurine, histidine, alanine, valine, cysteine, trihydroxymethylaminomethane (TRISTA) and triethanolamine. These bases are used in amounts which are sufficient to bring the pH of the emulsion to 5 to 7, which is close to the pH of the skin. The composition is therefore very compatible with the skin. In addition to the above-mentioned salicylic acid derivative, the composition of the invention contains an extract of mulberry, advantageously an extract of the root of Morus alba, or a substance isolated from such an extract, preferably a kuwanone or a derivative thereof. Processes for isolating kuwanone E are described, for example, in *Chemical Abstracts,* Vol. 89, 1978, abstract 89:211925f and in *Heterocycles,* Vol. 9, No. 9, 1978.

The composition also contains an extract of skullcap, advantageously an extract of the root of *Scutellaria baicalensis*, or a substance isolated from such an extract, preferably baicaline.

The extracts mentioned above can be prepared by extraction of plant material employing an aqueous, alcoholic or organic solvent, according to any extraction method known to those of skill in the art.

The term "aqueous solvent" means any solvent consisting totally or partly of water. Water itself may be employed or an aqueous-alcoholic solvent in any proportion or a solvent consisting of water and another compound such as propylene glycol or butylene glycol in any proportion.

A preferred alcoholic solvent is ethanol.

A preferred aspect of the invention is the use of extracts of plants obtained by extraction of plant material with an aqueous-alcoholic solvent, advantageously extracts containing 0.5–1.5% active material in 50% water and 48.5–49.5% butylene glycol.

Regardless of the method of preparation employed, subsequent steps directed to promoting the storage and/or stabilization of the composition may be added without modifying the actual nature of the extract. Thus, for example, the extract obtained can be freeze-dried by any standard freeze-drying method. A powder is thus obtained which can be used directly or otherwise mixed into a suitable solvent before use.

The amount of salicylic acid derivative and of extracts of mulberry and of skullcap present in the composition of the invention obviously depends on the desired whitening or depigmenting effect and may consequently vary within a wide range. In a preferred embodiment, the composition of the invention contains from 0.1 to 5% by weight, advantageously from 1 to 2% by weight, of salicylic acid derivative and from 0.1 to 20% by weight, advantageously from 0.5 to 1.5% by weight, of each of the extracts of mulberry and skullcap, relative to the total weight of the composition.

The composition of the invention is suitable for topical use and thus contains a cosmetically or dermatologically acceptable medium, i.e. a medium which is compatible with the skin, head hair or other hair.

The composition of the invention may be in any acceptable pharmaceutical form normally used for a topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, it being possible for these spherules to be polymer nanoparticles such as nanospheres and nanocapsules, or better still lipid vesicles of ionic and/or nonionic type.

The composition may be relatively fluid and may have the appearance of a white or colored cream, an ointment, a milk, a lotion, a serum, a paste or a foam. It may optionally be applied to the skin or to the hair in the form of an aerosol. It may also be in solid form, for example, in the form of a stick. It may be used as a care product and/or as a make-up product. It may also be in the form of a shampoo or a conditioner.

In a known manner, the composition of the invention may also contain the usual adjuvants in the cosmetic and dermatological fields such as hydrophilic and lipophilic gelling agents, hydrophilic and lipophilic active agents, preserving agents, antioxidants, solvents, fragrances, fillers, sunscreens, pigments, odor absorbers and dyestuffs. The amounts of these various adjuvants are those conventionally used in the fields considered, and, for example, from 0.01 to 20% of the total weight of the composition. According to their nature, these adjuvants may be introduced into the fatty phase, into the aqueous phase, into the lipid vesicles and/or into the nanoparticles.

Needless to say, it is obvious to a person skilled in the art that the active or non-active compounds which may be added to the composition are selected so as not to contravene the desired objective of the invention.

When the composition of the invention is an emulsion, the proportion of the fatty phase may range from 5 to 80% by weight, and preferably from 5 to 50% by weight, relative to the total weight of the composition. The oils, the emulsifiers and the co-emulsifiers employed in the composition in emulsion form are selected from those conventionally used in the field considered. The emulsifier and the co-emulsifier are present in the composition in a proportion ranging from 0.3 to 30% by weight, and preferably from 0.5 to 20% by weight, relative to the total weight of the composition.

Suitable oils which can be used in the invention include mineral oils such as liquid petrolatum, oils of plant origin such as avocado oil and soya oil, oils of animal origin such as lanolin, synthetic oils such as perhydrosqualene, silicone oils such as cyclomethicone and fluoro oils such as perfluoropolyethers. Fatty alcohols such as cetyl alcohol, fatty acids and waxes such as carnauba wax and ozocerite can also be used as fatty substances.

Suitable emulsifiers and co-emulsifiers which can be used in the invention include, for example, fatty acid esters of polyethylene glycol such as PEG-20 stearate, and fatty acid esters of glycerol such as glyceryl stearate.

Suitable hydrophilic gelling agents include, in particular, carboxyvinyl polymers such as carbomers, acrylic copolymers such as acrylate/alkylacrylate copolymers, polyacrylamides, polysaccharides, natural gums and clays. Suitable lipophilic gelling agents include modified clays such as bentones, metal salts of fatty acids, hydrophobic silica and polyethylenes.

Polyols, vitamins, keratolytic and/or desquamating agents, anti-inflammatory agents, calmants and mixtures thereof are particularly useful as active agents. Other depigmenting agents such as kojic acid or hydroquinone and its derivatives also may be added to the composition of the invention, making it possible to use these agents in smaller doses. When they are incompatible, at least some of these active agents may be incorporated into spherules, in particular ionic or nonionic vesicles and/or nanoparticles (nanocapsules and/or nanospheres), so as to isolate them from each other in the composition.

UV screening agents of lipophilic or hydrophilic nature such as benzene-1,4-bis(3-methylidene-10-camphorsulfonic acid), 2-ethylhexyl α-cyano-β,β-diphenylacrylate or octocrylene, butylmethoxydibenzoylmethane, octyl methoxycinnamate and/or titanium oxide or zinc oxide, may also be used in these compositions.

These compositions constitute in particular protective, treatment or care creams for the face, for the hands or for the body, body milks for care or protection, lotions, gels or mousses for skin care or skin treatment, cleansing or disinfecting lotions, bath compositions, foundations and tinted creams. In the latter cases, the composition contains pigments.

The composition defined above can be used for depigmenting and/or whitening human skin and/or for removing skin pigmentation marks and/or for depigmenting head hair and/or other hairs or for inhibiting the activity of tyrosinase and/or melanin synthesis.

An aspect of the invention is a cosmetic process for depigmenting and/or whitening human skin, head hair and/or other hairs, which consists of applying a composition of the invention to the skin, head hair and/or other hair.

Having generally described this invention, a further understanding can be obtained by reference to certain specific examples which are provided herein for purposes of illustration only and are not intended to be limiting unless otherwise specified. The concentrations given below are percentages by weight.

EXAMPLE 1

Preparation of a Composition

The following composition was prepared:

| | | |
|---|---|---|
| A | Glucate SS [Amerchol] (methyl glucose sesquistearate) | 1.5% |
| | Fatty alcohols | 4% |
| | Cyclomethicone | 5% |
| | 5-n-Octanoylsalicylic acid | 0.5% |
| | Octocrylene (Uvinul N539) | 2% |
| | Preserving agents | 0.1% |
| | Fragrance | 0.2% |
| B | Water | qs 100 |
| | Glycerol | 3% |
| | Glucamate SSE-20 [Amerchol] (PEG-20 methyl glucose sesquistearate) | 1.5% |
| | Preserving agents | 0.5% |
| C | Water 15% | |
| | Xanthan gum | 0.1% |
| | Aqueous-alcoholic extract of mulberry roots (containing 1% active material) | 1% |
| | Aqueous-alcoholic extract of skullcap (containing 1% active material) | 1% |
| D | Sepigel 305 (SEPPIC) | 1% |

Phase A is heated to 75° C. until fully dissolved, as is phase B. Phase A is introduced into phase B with stirring, until a fine, uniform emulsion is obtained. Phase C is homogenized with stirring in water at 40° C. and then introduced with stirring at 40° C. into the mixture A+B. Phase D is introduced at 40° C. and dispersed with stirring. The fluid obtained is cooled with stirring.

A fluid emulsion with depigmenting properties is obtained.

EXAMPLE 2

Evaluation of the Depigmenting Effect of the Composition of Example 1

Depigmenting activity of the composition of Example 1 was demonstrated on a model of human skin kept alive.

To do this, a sample of human skin of phototype IV is obtained by plastic surgery. The skin fragments are kept alive ex vivo by organ culture, i.e. they are placed in inserts suspended above culture wells and kept alive by means of a culture medium deposited at the base of the wells. The culture medium is refreshed three times a week.

The products below are applied once a day to the above fragments, at a rate of 2 mg/cm$^2$ of skin, five days a week for 21 days:

Product A: The excipient
Product B: The excipient+0.5% of 5-n-octanoyl-salicylic acid
Product C: The excipient+1% of plant extracts (mulberry+skullcap)
Product D: The excipient+0.5% of 5-n-octanoyl-salicylic acid+1% of plant extracts (composition of Example 1)

For comparative purposes, an untreated skin fragment is also kept alive under the same conditions.

After 21 days, a quantitative evaluation of the percentage of basal cells (keratinocytes and melanocytes) containing grains of melanin is performed histologically by optical microscope, on five fields, at +40 magnification, after staining with hemalum-eosin (Fontana method).

Three categories of cells are counted:
Score 1: mildly pigmented or unpigmented cells
Score 2: moderately pigmented cells, i.e. cells with a moderate melanin content (scattered grains of melanin, non-uniform deposition)
Score 3: highly pigmented cells, i.e. cells with a large content of melanin (uniform deposition covering more than half of the cytoplasm of the cells).

The results are collated in Table 1 below.

TABLE 1

|  | Score 1 (%) | Score 2 (%) | Score 3 (%) |
| --- | --- | --- | --- |
| Untreated skin | 5 | 34 | 67 |
| Skin treated with product A | 3 | 26 | 70 |
| Skin treated with product B | 4 | 30 | 66 |
| Skin treated with product C | 5 | 33 | 62 |
| Skin treated with product D | 10 | 51 | 39 |

A melanin index is calculated from this count according to the formula $$MI = 1 \times (\text{score } 1) + 2 \times (\text{score } 2) + 3 \times (\text{score } 3).$$

From this index, it is possible to calculate the percentage of inhibition of melanin:

$$\% \text{ inhibition} = MI(Te) - MI(Tr)/MI(Te) \times 100$$

in which:
MI (Te) denotes the melanin index of untreated skin;
MI (Tr) denotes the melanin index of skin treated with the test product A, B, C or D.

The results are collated in Table 2 below.

TABLE 2

|  | Melanin index | % inhibition |
| --- | --- | --- |
| Untreated skin | 274 | — |
| Skin treated with product A | 265 | 3 |
| Skin treated with product B | 262 | 4 |
| Skin treated with product C | 257 | 6 |
| Skin treated with product D | 229 | 16 |

There is no appreciable difference between the untreated skin and the skin treated with products A, B and C.

On the other hand, compared with the untreated skin or the skin treated with products A, B and C, the composition of the invention makes it possible to significantly reduce the number of highly pigmented cells, to increase the number of moderately pigmented cells and thus to obtain a degree of inhibition of melanin of 16%.

The disclosure of French priority application serial number 9812747 filed Oct. 12, 1998 is hereby incorporated by reference into the present application.

Obviously, numerous modifications and variations of the present invention are possible in light of the above teachings. It is therefore to be understood that within the scope of the appended claims, the invention may be practised otherwise than as specifically described herein.

What is claimed as new and is intended to be secured by letters patent is:

1. A cosmetic or dermatological composition, comprising: in combination, at least one extract of mulberry or an active substance isolated from said extract, at least one extract of skullcap or an active substance isolated from said extract, and at least one salicylic acid derivative of formula (I) or a salt thereof:

(I)

wherein R is hydrogen or a saturated or unsaturated, linear, branched or cyclic aliphatic, alkoxy, ester or ketoxy chain containing from 2 to 22 carbon atoms and optionally substituted with at least one substituent selected from the group consisting of halogen, trifluoromethyl and hydroxyl in free form or esterified with an acid containing from 1 to 6 carbon atoms or with a carboxyl group which is free or esterified with a lower alcohol containing from 1 to 6 carbon atoms; and R' is a hydroxyl group or an ester function of the formula:

$$-O-\underset{\underset{O}{\|}}{C}-R_1$$

wherein $R_1$ is a saturated or unsaturated aliphatic group containing from 1 to 18 carbon atoms, the combination exhibiting increased depigmentation and melanin inhibition activity in comparison to the depigmentation and melanin inhibition effects of the salicylic acid derivative and combined extracts applied separately to the skin.

2. The composition according to claim 1, wherein the salicylic acid derivative is selected from the group consisting of salicylic acid, 5-n-octanoylsalicylic acid, 5-n-decanoylsalicylic acid and 5-n-dodecanoylsalicylic acid.

3. The composition according to claim 2, wherein the salicylic acid derivative is 5-n-octanoylsalicylic acid.

4. The composition according to claim 1, wherein said salicylic acid compound or salt thereof is present in a concentration ranging from 0.1 to 5% by weight, relative to the total weight of the composition.

5. The composition according to claim 4, wherein said salicylic acid compound or salt thereof is present in a concentration ranging from 1 to 2% by weight.

6. The composition according to claim 1, wherein said at least one extract is an aqueous-alcoholic extract.

7. The composition according to claim 1, wherein said extract of mulberry is an extract of the roots of *Morus alba*.

8. The composition according to claim 1, wherein said extract of skullcap is an extract of the roots of *Scutellaria baicalensis*.

9. The composition according to claim 1, wherein the composition contains from 0.1 to 20% by weight of each of said extracts, relative to the total weight of the composition.

10. The composition according to claim 1, wherein the composition contains from 0.5 to 1.5% by weight of each of said extracts.

11. The composition according to claim 1, wherein said active substance isolated from the extract of skullcap is baicaline.

12. The composition according to claim 1, wherein said substance isolated from the extract of mulberry is kuwanone or a derivative thereof.

13. The composition according to claim 1, which further comprises a cosmetically and/or dermatologically acceptable medium.

14. A method of cosmetically treating the human skin and/or hair, comprising:

topically applying the cosmetic composition of claim 1 to the skin and/or hair, thereby depigmenting and/or whitening human skin and/or removing skin pigmentation marks.

15. A method of inhibiting tyrosinase activity or melanin synthesis, comprising:

applying the composition of claim 1 to the skin thereby inhibiting tyrosinase activity and/or melanin synthesis.

16. A method of dermatologically treating the human skin and/or hair, comprising:

topically applying the composition of claim 1 to the skin and/or hair, thereby depigmenting and/or whitening human skin and/or removing skin pigmentation marks.

* * * * *